United States Patent [19]

Reinhard et al.

[11] Patent Number: 5,340,836
[45] Date of Patent: Aug. 23, 1994

[54] COMPOSITION AND METHOD FOR TREATMENT OF VAGINAL YEAST INFECTIONS

[75] Inventors: Mark S. Reinhard, 1148 Tillers Ridge Drive, Richmond, Va. 23235; Byron T. Burlingham, Greenville, N.C.

[73] Assignee: Mark S. Reinhard, Richmond, Va.

[21] Appl. No.: 892,615

[22] Filed: Jun. 1, 1992

Related U.S. Application Data

[63] Continuation of Ser. No. 657,522, Feb. 19, 1991, abandoned.

[51] Int. Cl.$^5$ .............. A61K 31/045; A61K 31/70; A61K 31/495; A61K 31/50; A61K 31/415; A61K 31/19
[52] U.S. Cl. ......................... 514/557; 514/31; 514/396; 514/399; 514/252; 514/738
[58] Field of Search ................. 514/557, 738, 31, 252, 514/396, 399

[56] References Cited

U.S. PATENT DOCUMENTS

| | | | |
|---|---|---|---|
| T937,001 | 8/1975 | Baker | 424/343 |
| 2,333,124 | 7/1941 | Robertson et al. | 514/738 |
| 2,467,884 | 4/1949 | Elias | 167/58 |
| 3,384,541 | 5/1968 | Clark | 167/58 |
| 3,821,413 | 6/1974 | Hellyer | 424/343 |
| 3,836,672 | 9/1974 | Wright | 424/343 |
| 3,970,759 | 7/1976 | Frankenfeld | 424/343 |
| 4,294,852 | 10/1981 | Wildenauer | 424/317 |
| 4,310,510 | 1/1982 | Sherman | 424/45 |
| 4,788,060 | 11/1988 | Endicott et al. | 424/443 |

OTHER PUBLICATIONS

Eur. J. Biochem. 5 (1968):165; (Gancedo et al.).
Protoplasma 92 (1973): 177j Niedermeyer et al.
CA 83:162163w, Tseng et al., 1975.
CA 102:147653y, Yamamoto et al., 1984.

Primary Examiner—Marianne M. Cintins
Assistant Examiner—Kimberly R. Jordan
Attorney, Agent, or Firm—Olive & Olive

[57] ABSTRACT

A composition for the treatment of vaginal yeast which promotes normal vaginal bacterial growth during treatment, comprising a yeast-inhibitory agent selected from one or more of the group consisting of ethylene glycol, propylene glycol, and glycerol, and an effectively buffered aqueous acetate solution, in which the concentration of acetate is effective to establish a pH of the composition in the range of from about 5 to about 7, the presence of unionized acetate inhibits yeast selectively compared to the bacteria, and the proportions of the yeast-inhibitory agent and the buffering solution are effective to allow the active yeast-inhibitory agent to inhibit the vaginal yeast Candida. A method of treatment of vaginal yeast while promoting normal vaginal bacterial growth, by intravaginal application of the composition described above, is also disclosed.

19 Claims, 4 Drawing Sheets

COMPOSITION AND METHOD FOR TREATMENT OF VAGINAL YEAST INFECTIONS

This application is a continuation of U.S. Ser. No. 07/657,522, filed Feb. 19, 1991, now abandoned.

BACKGROUND OF THE INVENTION

1. Field of the Invention

This invention relates generally to compositions having utility for the treatment of vaginal yeast while promoting normal bacterial growth, and to a method of treatment of vaginal yeast conditions.

2. Description of the Related Art

Yeast infections, also termed Candidiasis, moniliasis, or Monilia vaginitis, are among the most frequently occurring of vaginal infections. These vaginal infections are caused by fungus-like yeasts of the genus Candida (formerly Monilia), and specifically the species including *C. albicans*, *C. tropicalis*, *C. psuedotropicalis*, and *C. stellatoidea*. These Candida fungal microorganisms, also known as Monilia, normally grow and thrive at low concentrations in the mouth, gastrointestinal tract, and vagina, coexisting with the normal biological flora in these regions, without adverse effect on health or physiological function.

In the vagina, the homeostasis between these Candida fungi and the normal vaginal flora nonetheless may be upset by changes in vaginal pH, or other conditions upsetting the vaginal equilibrium or otherwise lowering resistance to infection. Monilia overgrowth then may occur, resulting in a thick, white colored vaginal discharge which often is likened to cottage cheese in consistency, and associated with a strong odor. This condition occurs frequently in women during pregnancy, or as a result of conditions such as diabetes, treatment with antibiotics, steroids or immunosuppressive therapy, or hormonal changes occurring during the menstrual cycle.

The two major classes of antifungal agents employed are the polyenes (nystatin and amphotericin) and the imidazole derivatives (miconazole, clotrimazole, butuconazole, and ketoconazole).

Over the counter preparations for vaginal cleaning and deodorization generally contain glacial acetic acid and water and may contain glycerin and various thickening agents. Although vinegar douches comprising a solution of vinegar and water have been commonly employed for many years for cosmetic douching purposes, and are often resorted to for flushing yeast deposits and bacteria from the Monilia-infected vagina, such methods do not in fact destroy the Candida fungi in situ. The pH of these products are all at or below 3.5 when measured on a pH meter. The normal vaginal pH is approximately 4.5 and this homeostatic condition is not significantly altered by vinegar douching. Vinegar douching treatment has been predicated on the incorrect belief that lower pH values in the vagina promote the growth of normal vaginal flora at the expense of Candidal fungal species. In the vaginal pH range, the pathogenic yeasts compete with normal bacterial flora, displacing or suppressing the growth of biota needed for healthy vaginal functioning.

More effective treatment of Candida infections typically involves the application of an anti-yeast medication to the vagina, with intravaginal administration of medicine being repeated at selected intervals over a period of days or weeks.

An example of an intravaginally applied medication is a water miscible cream composition containing 2% by weight 1-2,4-dichloro-beta-(2,4-dichlorobenzyloxy) phenethyl] imidazole nitrate in a cream base comprising mineral oil, pegoxol-7 stearate, peglicol-5-oleate, butylated hydroxyanisole, benzoic acid, and water, commercially available from Ortho Pharmaceutical Corporation, Raritan, N.J., under the trademark MONISTAT 7. This composition is recommended by the manufacturer to be applied intravaginally once daily for 7 days.

It is an object of the present invention to provide a Candidastatic and/or Candidacidal composition which promotes a high rate of growth of normal vaginal biota during treatment, while selectively inhibiting the growth, reproduction and germination of Candida organisms in the vagina.

Other compositions used to treat Candida, and other uses for the components or related components of Applicant's composition are discussed below.

U.S. Defensive Publication T937,002 of N. G. Baker discloses the treatment of ungulate mastitis, a bacterial infection, with glycols having 3 to 4 carbon atoms and at least one terminal group, e.g., 1,3-butylene glycol, administered in pharmacologically effective doses. The disclosure of this reference and of all others cited herein is incorporated herein by reference.

U.S. Pat. No. 4,310,510 to K. N. Sherman, et al. discloses an intravaginally applied anti-fertility composition comprising a foamable aqueous emulsion containing progesterone as the active ingredient. The Sherman, et al. patent at column 8, lines 48–68 discloses that the formulation, in addition to progesterone and an anionic surfactant, may contain buffering agents such as phosphates, citrates or tartrates, to maintain a pH in the range normal in the female genital tract, that is on the order of about 4.5 in the vagina. In a preferred disclosed embodiment, the composition contains 10–50% by weight of a lower glycol as a foam stabilizer, the patent stating that in such concentration range, the glycols prevent microbial growth in the formulation so that preservatives are not required. In addition, other foam stabilizers may be substituted for glycols, such as glycerol and the polyalkylene glycols, such as polypropylene glycol and polyglycerols.

Among the progesterone compounds useful in the practice of Sherman's antifertility composition (column 6, lines 11–30 of Sherman) are various progestin acetate compounds. There is no indication in Sherman of any Candidacidal activity of glycols and/or a non-steroid acetate compound nor of their use in the absence of progesterone and anionic surfactants.

U.S. Pat. No. 3,970,759 to J. W. Frankenfeld, et al. discloses the inhibition of bacteria, yeasts, and molds in cosmetic personal care compositions containing edible oils and organic nitrogen compounds, by incorporating therein an effective amount of a linear aliphatic 1,3-diol, or a monoester or diester thereof. The diols disclosed as suitable for this purpose contain 5–15 carbon atoms in the chain; suitable diesters have a linear aliphatic acyl group of 2–20 carbons.

U.S. Pat. No. 4,294,852 to R. H. Wildnauer, et al. discloses a topically applied skin composition for treatment and control of dry skin disorders, comprising an aqueous phase in which is dissolved one or more specified aliphatic alcohols in combination with one or more selected aliphatic mono, di- or tri- carboxylic acids having 2–10 carbon atoms, including those which are substituted at either or both of the alpha and beta carbons with a hydroxyl or keto functional group.

The Wildnauer, et al. patent discloses at column 5, lines 6–7 that the disclosed composition may comprise propylene glycol as an additive. Propylene glycol is also mentioned in the same column at lines 17 et seq. as an active compound with which the disclosed composition may be employed as a vehicle. Other such active ingredients include dexamethasone acetate and anti-fungal agents such as griseofulvin, Mycostatin TM, miconazole and minconazole nitrate. Among the alpha, beta-dihydroxy carboxylic acids disclosed in the patent are glyceric acid; the disclosed keto acids include glyoxylic acid, pyruvic acid and acetoacetic acid.

U.S. Pat. No. 3,836,672 to D. D. Wright, et al. discloses the treatment of bacterial and fungal infections by linear diols and/or their mono-esters, the diols containing 7–15 carbons and hydroxy groups on the first and third carbon atoms while the mono-esters have acyl groups of 2–10 carbons.

The Wright, et al. patent discloses in the paragraph bridging columns 4 and 5 that Monilial vaginitis caused by *Candida albicans* is treated to control the fungal organism with minimum disturbance of the normal vaginal bacterial flora. A 50-50 mixture of 1,3-nonanediol and 1,3-butanediol monooctanoate is disclosed as effective for the treatment of fungal vaginitis, and as being effective against fungi at levels where it is only mildly inhibitory to bacteria. The patent at column 6, lines 30–38 describes inert carriers for the disclosed compositions, including glycerol as an inert carrier for providing a paste or cream-like consistency, or propylene glycol or ethylene glycol as an inert carrier for propellant type or aerosol materials.

U.S. Pat. No. 3,821,413 to H. L. Hellyer, Jr., discloses atmospheric germicidal compositions comprising from about 5–85% by weight of a glycol germicide, e.g., ethylene glycol, or propylene glycol, from 2–40% by weight of an organic polar coupling compound including various specified alcohols such as beta-phenylethyl alcohol and alphaterpineol, and from about 5–80% by weight of an organic, relatively non-polar compound for forming hydrophobic micelles surrounding the glycol molecules in the mixture to reduce the glycol affinity to atmospheric moisture. The non-polar compounds disclosed in the patent at column 2, lines 54–58 include various acetate compounds such as benzyl acetate, citronellyl acetate, octyl acetate, and 1,3-nonanediol acetate.

U.S. Pat. No. 3,384,541 to W. G. Clark discloses a spermicidal vaginal foam-producing composition comprising ethoxylated tallow alcohol, propylene glycol or other glycols or glycerol. The patent discloses to utilize such composition in combination with a buffered fructose solution. Example 23 of the patent teaches to add iodine compounds to the composition for the treatment of vaginitis, and *Candida albicans*, Monilia, and *Trichomonas vaginalis*, along with the contraceptive function of the composition.

U.S. Pat. No. 2,451,955 to H. Keil, et al. discloses the use of a composition to determine susceptibility to dermatitis, comprising a solution of a synthetic vicinal alkyl pyrocatechol with 10–18 carbons in the alkyl group, in a non-irritant organic solvent such as iso-amyl acetate, a water insoluble acetate ester.

U.S. Pat. No. 2,467,884 to N. N. Elias discloses spermicidal compositions comprising neutral aliphatic hydroxy compounds such as higher fatty alcohols, hydroxyethers, hydroxyesters and hydroxyester ethers. The composition may comprise an aqueous vehicle containing a water soluble acid for bringing the pH of the resulting composition within the range of 1–7. The patent discloses that the pH is established by means of whatever simple organic or inorganic acids and buffer salts may seem desirable. The patent discloses that glycerine may be added to the spermicidal compositions to prevent their dehydration and freezing. The patent also discloses the use of water soluble acids such as acetic acid, with potassium acetate and sodium acetate being disclosed as buffers.

When Saccharomyces yeast cells are incubated in hypertonic glycerol solutions, the cells shrink to about 40% of their original volume with glycerol premeating the cells resulting in alteration of membrane morphology. The shrinking is reversible upon removal from the 8.7% glycerol solution but incubation in solutions above 17.4% glycerol is lethal for exponentially growing yeasts. Protoplasma 92:177 (1977).

Glycerol is also known to be metabolized by yeasts as Candida and Saccharomyces and is a by-product of some yeast metabolism. See European J. Biochem 5:165 (1968).

SUMMARY OF THE INVENTION

In a broad aspect, the invention relates to a composition having utility for the treatment of vaginal yeast while promoting normal vaginal bacterial growth, comprising a solution comprising one or more medically acceptable agents, said agents selected from the group consisting of ethylene glycol, propylene glycol, glycerol, acetate derivatives of glycerol, and acetate; said solution having active yeast inhibitory activity and being effectively buffgred to establish the pH of the composition at about neutral.

In a narrower aspect, the present invention relates to a composition having utility for the treatment of vaginal yeast while not adversely affecting normal vaginal bacterial growth, comprising:

(a) a medically acceptable active yeast-inhibitory agent selected from one or more members of the group consisting of ethylene glycol, propylene glycol, and glycerol, having an effective concentration at the vaginal treatment site of at least 8% by volume of the composition volume plus the volume of other liquids present at the treatment site; and (b) an effectively buffered aqueous acetate solution constituting 92% or less by volume of the composition;

wherein the concentration of acetate in said effectively buffered aqueous solution is effective to establish the pH of the composition in the range from about 5.0 to about 7, and wherein the active yeast-inhibitory agent and said effectively buffered aqueous acetate solution are in selected proportions relative to one another effective to allow the active yeast-inhibitory agent to be inhibitory against vaginal yeast of the genus Candida.

The composition may further comprise an antibiotic such as Nystatin, imidazoles or others, in addition to the medically acceptable agents, for example, in addition to the active yeast-inhibitory agent and the acetate solution.

In another aspect the invention relates to a method for treatment of vaginal yeast while not adversely affecting normal vaginal bacterial growth, comprising applying to the vaginal locus a buffered solution of a yeast-inhibitory agent in an amount effective to inhibit Candida, said yeast-inhibitory agent selected from one or more members of the group consisting of ethylene glycol, propylene glycol, and glycerol, said solution buffered to maintain the vaginal pH in the range of from about 5 to about 7, for sufficient time to permit the yeast-inhibitory agent to inhibit the vaginal yeast while permitting normal bacterial growth to occur in the vaginal locus, and permitting the vaginal bacteria to consume vaginal nutrients and competitively inhibit growth of yeasts.

The invention also comprises a method of allowing normal vaginal flora to be restored, comprising douching with a buffered solution of a yeast-inhibitory agent, said yeast-inhibitory agent selected from one or more members of the group consisting of ethylene glycol, propylene glycol, and glycerol, said solution buffered to maintain the vaginal pH in the range of from about 5 to about 7, for sufficient time to permit flushing of the vagina while promoting normal bacterial growth in the vagina; and a method of allowing normal vaginal flora to be restored, comprising douching with an effectively buffered aqueous acetate solution, said solution buffered to maintain the vaginal pH in the range of from about 5 to about 7, for sufficient time to permit flushing of the vagina while encouraging normal bacterial growth in the vagina. Applying to the vaginal locus an amount of the above-described composition effective to inhibit Candida.

The inhibition of Candida comprises a static effect at lower concentrations of glycol or glycerol and a cidal effect at concentrations near or above 40%. The term "inhibit", "inhibitory" or "inhibition" herein means decreasing the rate of growth and shall also include any killing of yeast cells that may occur at higher concentrations and/or less desirable growth conditions for the Candida.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
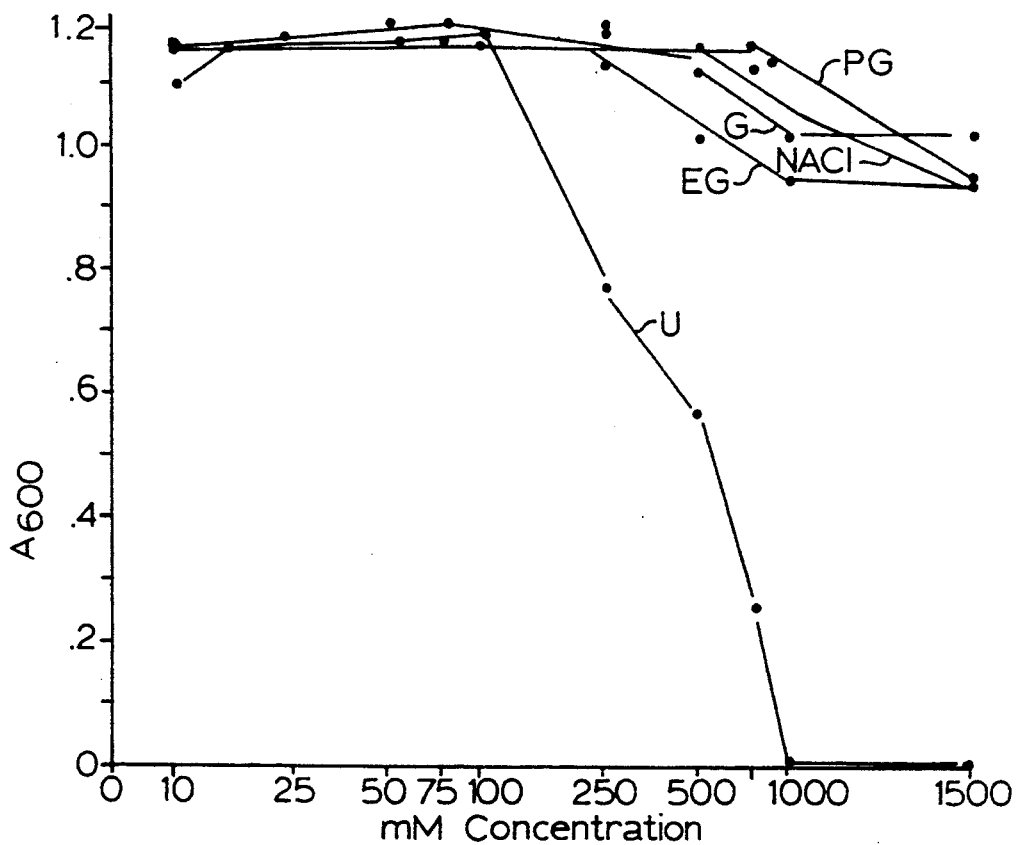
FIG. 1 is a graph of optical density ($A_{600}$) of Lactobacillus versus mM concentration of propylene glycol (PG), urea (U), ethylene glycol (EG), and NaCl (NaCl).

The present invention is based on the fact that the normal pH balance of the vagina, being typically slightly acidic on the order of pH 4.5, is a homeostatic condition with respect to the populational dynamics of normal vaginal biota. As indicated hereinabove in the "Background of the Invention" section hereof, the prior work in the treatment of Candida infections has typically sought to effect vaginal treatment at the normal vaginal pH acidic conditions, on the theory that compositions which were inhibitory or cidally effective against Candida at such normal pH conditions would permit the normal vaginal biota to be reestablished concurrent with the destruction of the fungal infection.

The present invention is based on the discovery that growth of vaginal biota concurrent with destruction of Candida organisms is best effected at a neutral pH, inasmuch as the rate of growth of normal vaginal biota is substantially higher at such elevated pH conditions than at the lower pH values characteristic of the healthy vagina at equilibrium. The composition of the invention is based on the surprising finding that with the composition of the invention, a succession of environmental changes in the vagina provides maximum yeast inhibition while enhancing growth of the normal vaginal flora. Thus, laboratory work shows that the glycol compounds such as glycerol, propylene glycol and ethylene glycol, which are nontoxic to human cells and bacteria, inhibit the yeast at the initial roughly neutral pH of the composition (e.g. above pH 4.5, preferably about pH 5 to pH 7, and most preferably at about pH 7.0). As bacterial growth occurs, vaginal nutrients are consumed, and the pH decreases, the acetate component of the composition inhibits the yeast to a greater extent than it inhibits the normal vaginal bacterial population.

Accordingly, the compositions of the invention effect destruction of the yeast organisms by being biostatically or biocidally effective against Candida at a neutral pH secured by an appropriately constituted aqueous acetate buffer solution. Thus, the topical application of compositions of the invention to the vaginal locus will expose the vaginal tissue to a neutral pH where growth of normal vaginal biota is promoted, concurrent with the inhibition of the undesired Candida organisms.

Concurrent with this accelerated growth of the desired normal vaginal biota at neutral pH, the Candida and other yeast species are similarly metabolically accelerated, to the extent that such organisms are not killed by the active yeast-inhibitory component of the composition of the invention. While it may be initially thought that such acceleration of the metabolic growth rate of the yeast species would be deleterious in the sense that an increased population would require cidal action by the composition, the results support the conclusion that the metabolic byproducts of such yeast organisms include metabolites such as glycerol, and glycols, e.g., ethylene glycol and propylene glycol, which themselves are biostatically or biocidally effective against the Candida and potentially other yeast species. Thus, the undesired yeast growth may be effectively poisoned by its own metabolic end products, in combination with similar external end products of the normal vaginal microorganisms. In fact, in the population growth of such yeast species in culture, the population in a nutrient-rich solution of constant concentration will experience log growth to a point of metabolic homeostasis, where the available nutrients and deleterious metabolites come into equilibrium with one another, followed by declining microbial concentration as the metabolites accumulate and reduce the population.

Thus, results indicate that the accelerated production of metabolic byproducts as effective species in inhibiting Candida generated in situ in the vaginal environment, in combination with the fungistatic/fungicidal action of the composition of the invention, produces a highly effective treatment of the Candida organisms and other yeast species, resulting in their control and/or destruction.

With this bifurcated action against the vaginal yeast, the pH conditions maintained by the acetate buffer promote the growth of normal vaginal flora. As such normal flora proliferates, the metabolic waste products of the normal vaginal flora, which may include the aforementioned metabolic byproducts effective against the Candida and other yeast species, gradually accumulate to overcome the buffering action of the composition, and return vaginal acidity to normal pH conditions.

As the buffering action is overwhelmed, and lower pH, in the range approaching normal acidity of about 4.5, is established, the acetate constituent of the buffering solution is increasingly nonionized (its ionization decreasing with decreasing pH), and the resulting increased concentration of acetic acid and other nonionizable esters of acetate, such pH equilibrium effects increase the inhibitory efficiency of the composition against the yeast. The extent of this ancillary inhibitory action of the composition at reduced pH values in the vicinity of normal vaginal pH is dependent on the specific acetate material utilized in the composition.

Generally, any suitable acetate compound may be employed as the acetate constituent of the buffer solution, including compounds of the formula $CH_3COOR$, wherein R is hydrogen or a lower alkyl. Among the various acetate compounds of such type, acetic acid ($CH_3COOH$) is preferred, followed by $C_1$–$C_3$ alkyl acetate compounds. Although any physiological inert buffer in the neutral pH range would promote normal vaginal flora growth, the present invention is directed in a preferred aspect to the use of acetate buffers, for the reason discussed above that they have an increased biological activity against Candida and other yeasts as vaginal pH is reduced to normal levels on the order of about 4.5.

Acetate compounds with which the acetate moiety is locked into a nonionized form may be used. For example, triacetin and diacetin (glycerol compounds esterified with acetic acid) are capable of serving both as the active yeast-destructive agent as well as the acetate source.

The active yeast-inhibitory agent, preferably as selected from one or more of ethylene glycol, propylene glycol, and glycerol, may in the broad practice of the invention preferably constitute from about 8% to about 40% by volume of the composition as delivered to the treated site, based on the total volume of the active yeast-inhibitory agent and the effectively buffered solution and any dilution of liquids in the administration of the agent. Higher concentrations are effective but may result in tissue irritation. The preferred concentrations provide effective Candida inhibition while not being irritating although higher concentrations also provide effective inhibition of Candida.

Correspondingly, the effectively buffered aqueous acetate solution may constitute from about 60% to about 92% by volume, on the same total volume basis. The concentration of acetate compound in the effectively buffered solution should be sufficient to establish the pH of the composition above 4.5, that is, above the normal vaginal pH. Preferably the pH of the composition is in the range of from about 5 to about 7, and the active yeast-inhibitory agent and buffering solution should each be in selected proportions relative to one another which are effective to allow the active yeast-inhibitory agent to be biocidally effective against Candida organisms. Most preferably, the pH is about neutral. A concentration of about 100 mM has been found to be effective.

It will be appreciated that more than one of the aforementioned active yeast-inhibitory compounds may be used in combination in compositions of the invention, e.g., a mixture of propylene glycol and glycerol.

While the concentrations of the glycol or glycerol component and the buffering acetate compound may be widely varied in the composition and relative to one another; within the foregoing functional constraints (i.e., the buffering solution being effective to establish a pH in the range of from about 5 to about 7, and the active yeast-inhibitory agent being in sufficient concentration and proportion relative to the buffering solution to allow it to be biostatically effective against the vaginal yeast), buffering solutions containing about 100 millimoles of acetic acid per liter in combination with propylene glycol present at a concentration of 1.0 to 1.5 Molar have been found to be generally effective Candidacidal compositions. Generally, glycerol when used as the active yeast-inhibitory agent may be used at preferred concentrations on the order of 1 Molar based on the total volume of the glycerol and the buffer solution. In the case of propylene or ethylene glycol, concentrations on the order of 1.5 Molar, on the same total volume basis, may be advantageously employed for killing yeast but may be unacceptably effective in also killing vaginal bacteria.

With reference to the glycolic yeast-inhibitory agents, as selected from one or more members of the group consisting of propylene glycol, ethylene glycol, and glycerol, all are polyhydroxy-functional compounds. It is possible that other active yeast-inhibitory agents may be employed in place of these compounds, to provide advantages similar to those observed with the above-described specific agents. Nonetheless, from the standpoint of physiological compatibility, and inhibitory activity, these materials are highly preferred.

It is to be understood that the composition of the invention has Candidacidal activity in the absence of any medically active or antibiotic compounds other than the acetate and glycol compounds, but other Candidacidal drugs may be added. Nystatin, a polyene antifungal antibiotic complex produced by various Streptomyces species which has been used to inhibit fungi and yeasts, or other anti-fungal agents, may be added to the composition of the invention to provide enhanced anti-Candida activity. Other fungal agents that may be added include, but are not limited to clotrimazol, miconazole, butoconazole and terconazole.

It is anticipated that in the use of the composition of the invention for Candidacidal treatment, the composition would not contain compounds unrelated to or unrequired for such treatments such as hormones, contraceptives, non-glycol alcohols, other organic molecules or antibacterial compounds which are not primarily Candidacidal, nor significantly larger glycol or acetate compounds.

The fungicidal or fungistatic compositions of the invention may additionally contain any suitable additives which do not preclude its yeast-inhibitory character and the neutral pH vaginal flora growth-promotion mechanism previously described. Illustrative of exemplary additives are stabilizers, extenders, antioxidents, perfumes, dyes, fillers, surfactants, etc.

In order to enhance the in vivo retention of the composition after its intravaginal application, the composition may suitably contain a pharmaceutically acceptable carrier, or a thickener, providing the composition with sufficient viscosity to be appropriately retained despite movement and position of the female to whom it has been administered. Suitable thickeners of such type may include materials such as hydroxypropylcellulose and/or hydroxypropylmethylcellulose. A particularly preferred thickener is carboxymethylcellulose, as commercially available under the trademark CARBOPOL® (Hercules Corporation, Wilmington, Del.).

As a class, nitrogen cross-linked carboxyl-containing thickeners are preferred. The addition of thickeners is highly desirable to provide the aforementioned retention function for the composition after its intravaginal administration. In the absence of such thickeners, or pharmaceutically acceptable carriers of other types, providing such viscosity and/or retention function, the composition may have to be applied more frequently than would be the case when a thickener or carrier is employed.

The composition of the invention may be applied to the vaginal area by any method known in the art, for example, as a sponge, as an osmotic device, as a douche, and so forth for treatment of vaginal yeast and to allow the normal flora to be maintained and the yeast population and growth to be repressed.

The features and advantages of the invention are more fully shown with respect to the examples set forth below. In these studies the composition of the invention is tested in laboratory tests in which the culture tube simulates the vagina.

In ovulating women, the age group which gets vaginitis, the vagina has a very thick, impervious layer of squamous epithelial cells, much like a glass wall of a culture tube. The vagina and cervix secrete very little fluid under normal conditions, thus there is no flow of material. There is usually only 1-2 ml of cervical secretion present and it is static much as the culture fluid is in a tube. The walls of the vagina are not rigid and thus collapse together in a convoluted shape that gives the vagina an enormous surface to volume ratio not present in a cylinder. But with no gas or fluid exchange due to the epithelium, this ratio is not relevant for these studies. The $O_2$ tension in the vagina and the culture tube are similar and undergo similar changes when bacteria and/or yeast are metabolizing the nutrient. Medium 19 used in nearly all of these studies has an electrolyte, protein and carbohydrate composition very similar to normal vaginal fluid. The experiments with added serum mimic and carry to about 4-fold excess any changes that might occur during any inflammatory exudation.

With respect to these examples as hereinafter set forth, the following methods and procedures were employed:

Isolation of Candida sp and Normal Vaginal Bacterial Flora from Clinical Specimens Specimens were collected from women clinically diagnosed as having Candida vaginitis at the Pitt County Health Department, Greenville, N.C. The presence of yeast was confirmed by microscopic examination of wet preparations by the staff at the Health Department. Specimens were also collected from asymptomatic women attending the Family Planning Clinic at the Pitt County Health Department. All specimens were submitted on Culturette® swabs and visibly contained exudates typically associated with Candida vaginitis. The specimens were streaked on chocolate agar, blood agar, and Sabouraud's dextrose agar, (peptone, 10 g; glucose, 40 g; agar 15 g; 1000 ml water; pH 5.6), with 40 μg/ml chloramphenicol. The specimens remaining on the swabs were incubated in trypticase soy broth. All cultures were incubated at 37° C. in 5% $CO_2$ atmosphere for 48 hr. Well isolated colonies were selected for subculture. After three cycles of subculturing, smears of the isolates were Gram stained, microscopically examined, and morphologically characterized. The isolated organisms were stored on slants at 4° C. until further characterized or used experimentally.

Medium 19

In the subsequent examples, Medium 19 refers to the nutrient composition set forth in Table I below.

TABLE I

| Peptone | 9.4 g |
|---|---|
| Yeast Extract | 4.7 g |
| Beef Extract | 2.4 g |
| NaCl | 10.0 g |
| Dextrose | 10.0 g |
| Agar | 23.5 g |
| Water qs | 1000 ml |
| pH 6.1 ± 0.1 after sterilization | |
| Medium 19 broth is Medium 19 with the Agar deleted. | |

Lactobacillus

The Lactobacillus species were grown in Lactobacilli MRS Broth purchased from Difco Laboratories, Detroit, Mich.

Growth Assay for Candida

A culture tube containing 10 ml Medium 19 broth was inoculated with *C. albicans* and incubated overnight at 37° C. Two drops of the heavy overnight growth were diluted into a fresh tube of Medium 19 broth and incubated at 37° C. until the yeast was in active logarithmic growth (about 4 hr). This logarithmic phase culture was diluted to $A_{600}=0.05$ in Medium 19 broth for use as experimental inoculum. As used herein, $A_{600}$ refers to the culture sample absorbance (turbidity) measured at 600 nanometers wavelength incident light, as passed through the sample and detected by a suitable photodetector.

The experimental tubes were prepared to contain a total volume of 9.9 ml medium and reagents. Then 0.10 ml of microbial inoculum was added. The inoculated medium was vigorously mixed, and then the tubes were incubated as stationary cultures at 37° C. for the duration of the experiment.

The amount of growth was determined turbidimetrically at appropriate intervals for 96 hours. The culture tubes were vigorously mixed to uniformly suspend the yeast. The turbidity was determined in 1 cm cuvettes at 600 nm.

Inoculated tubes with no increase in turbidity were subcultured by transferring 0.10 ml of the culture to 10 ml of fresh Medium 19 broth, incubating at 37° C. for 48 hours and recording the appearance of gross turbidity.

Growth Assays for Other Yeast and Bacteria

The growth assay of *S. cerevisiae* and all bacteria except Lactobacillus was assayed in a method parallel with *C. albicans*. All *S. cerevisiae* cultures were incubated at 25° C. Lactobacillus was cultured in MRS broth instead of Medium 19.

The features and advantages of the present invention will be more clearly understood by reference to the following examples, which are not to be construed as limiting the invention.

EXAMPLE I

Assay for Suppression by Glycerol, Glycols and Urea

A series of Medium 19 formulations was prepared containing either glycerol, ethylene glycol, propylene glycol, or urea as the supplement. The media were prepared from a stock of 2X Medium 19 broth and a 3M solution of the supplement. The supplement was diluted to a final concentration of 0 mM, 10 mM, 25 mM, 50 mM, 75 mM, 200 mM, 250 mM, 500 mM, 750 mM, 1.00M and 1.5M. The control cultures contained an iso-osmotic concentration of NaCl. All preparations of media were steam sterilized. One set of each medium was prepared for each organism. The media were inoculated with *C. albicans* (ATCC 14053, wt), *C. albicans* (ATCC 38247), *C. tropicalis, C. pseudotropicalis, C. stellatoidea, S. cerevisiae,* Streptococcus sp (ATCC 19950), *S. epidermidis,* or *E. coli.* The growth of the organisms was assayed as described in the growth assay for Candida.

A parallel assay was done for Lactobacillus sp (ATCC 9857) using MRS medium as a nutrient medium in place of Medium 19 Broth.

Assay data is presented in Table II below for each of the yeast-destructive agents glycerol, ethylene glycol, propylene glycol, and urea, and for the sodium chloride control. For the various molar concentrations of each, optical density values are shown at incubation times of 17, 46, 72, and 148 hours.

These data show that propylene glycol and urea were highly effective at concentrations on the order of 1.5M in suppressing the growth of *Candida tropicalis,* while ethylene glycol and glycerol were less effective against this Candidal species. Similar data were obtained for corresponding assays of *Candida albicans.*

These data also show that in some instances, e.g., in the case of propylene glycol and urea, increased incubation times and increased concentrations of the yeast-inhibitory agent coact to produce a highly effective removal of the undesired Candida species.

TABLE II

| YEAST DESTRUCTIVE AGENT: Incubation Times, Hrs. | GLYCEROL Concentration, mM | Optical Density | ETHYLENE GLYCOL Concentration, mM | Optical Density | PROPYLENE GLYCOL Concentration, mM | Optical Density | UREA Concentration, mM | Optical Density | NaCL CONTROL Concentration, mM | Optical Density |
|---|---|---|---|---|---|---|---|---|---|---|
| 17 | 0 | 1.213 | 0 | 1.149 | 0 | 1.262 | 0 | 1.13 | 0 | 1.115 |
| " | 100 | 1.103 | 100 | 1.073 | 100 | 1.147 | 100 | 1.151 | 125 | 1.057 |
| " | 1500 | .911 | 1500 | .631 | 1500 | .013 | 1500 | 0 | 750 | .822 |
| 4 | 0 | 1.422 | 0 | 1.415 | 0 | 1.463 | 0 | 1.349 | 0 | 1.474 |
| " | 100 | 1.542 | 100 | 1.453 | 100 | 1.397 | 100 | 1.263 | 125 | 1.359 |
| " | 1500 | 1.33 | 1500 | 1.253 | 1500 | 0 | 1500 | 0 | 750 | 1.263 |
| 72 | 0 | 1.631 | 0 | 1.616 | 0 | 1.673 | 0 | 1.57 | 0 | 1.661 |
| " | 100 | 1.851 | 100 | 1.769 | 100 | 1.641 | 100 | 1.447 | 125 | 1.545 |
| " | 1500 | 1.632 | 1500 | 1.177 | 1500 | 0 | 1500 | 0 | 750 | 1.484 |
| 148 | 0 | 1.756 | 0 | 1.736 | 0 | 1.694 | 0 | 1.794 | 0 | 1.789 |
| " | 100 | 2.051 | 100 | 1.882 | 100 | 1.85 | 100 | 1.592 | 125 | 1.791 |
| " | 1500 | 1.836 | 1500 | 1.655 | 1500 | 0 | 1500 | 0 | 750 | 1.711 |

TABLE III

| YEAST DESTRUCTIVE AGENT: Incubation Times, Hrs. | GLYCEROL Concentration, mM | Optical Density | ETHYLENE GLYCOL Concentration, mM | Optical Density | PROPYLENE GLYCOL Concentration, mM | Optical Density | UREA Concentration, mM | Optical Density | NaCL CONTROL Concentration, mM | Optical Density |
|---|---|---|---|---|---|---|---|---|---|---|
| 19 | 0 | .193 | 0 | .142 | 0 | .144 | 0 | .16 | 0 | .14 |
| " | 100 | .111 | 100 | .14 | 100 | .094 | 100 | .135 | 125 | .131 |
| " | 1500 | .029 | 1500 | .031 | 1500 | .019 | 1500 | 0 | 750 | .007 |
| 24 | 0 | .585 | 0 | .564 | 0 | .582 | 38 | .142 | 0 | .553 |
| " | 100 | .524 | 100 | .482 | 100 | .558 | 100 | .397 | 125 | .45 |
| " | 1500 | .085 | 1500 | .08 | 1500 | .033 | 1500 | 0 | 750 | .013 |
| 48 | 0 | 1.292 | 0 | 1.62 | 0 | 1.292 | 0 | 1.303 | 0 | 1.342 |
| " | 100 | 1.298 | 100 | 1.297 | 100 | 1.298 | 100 | 1.553 | 125 | 1.26 |
| " | 1500 | 1.075 | 1500 | 1.013 | 1500 | 549 | 1500 | 0 | 750 | .058 |
| 72 | 0 | 1.224 | 0 | 1.554 | 0 | 1.238 | 0 | 1.243 | 0 | 1.235 |
| " | 100 | 1.2 | 100 | 1.203 | 100 | 1.218 | 100 | 1.486 | 125 | 1.227 |
| " | 1500 | 1.096 | 1500 | 1.158 | 1500 | 1.024 | 1500 | 0 | 750 | .327 |

The corresponding assay for *S. cerevisiae,* as representative of the normal vaginal flora, is shown in Table III. This table is tabulated analogously with respect to Table II, except that the incubation periods in Table III were 19, 24, 48, and 72 hours.

The data in Table III shows that the metabolic by-product effect is significant in the case of normal vaginal flora as well as the undesired yeast species. To the extent that yeast species are present however, and are more affected by the yeast-inhibitory agent of the composition than the normal flora, the effects of byproduct-mediated reduction of this normal microbial population in the vagina will be significantly reduced.

Taken together, the data of Tables II and III show the suppressive effects of three byproducts compounds, glycerol, propylene glycol, and ethylene glycol, as compared with the suppressive effects of equimolar concentrations of urea and NaCl. The NaCl supplemented medium was included as a control to evaluate osmotic effects. As shown in Table III, NaCl did not affect the growth of either of the yeast organisms. Propylene glycol is a more potent inhibitor of yeast growth than ethylene glycol and glycerol was the least potent. Propylene glycol at 1.5M inhibited Candida. The other byproduct compounds were not inhibitory in the range assayed. Urea was an extremely potent inhibitor at >0.75M.

In corresponding tests, the bacteria were insensitive to glycerol, propylene glycol and ethylene glycol at lower concentrations but were sensitive to high concentrations of each (FIG. 1). The bacteria were less sensitive to the effects of urea than the yeasts. Lactobacillus sp (ATCC 9857) was the most sensitive of the bacteria tested. It was suppressed by the highest level of glycerol and ethylene glycol. Propylene glycol at >1.5M was inhibitory.

Glycerol suppresses growth of pathogenic, opportunistic and saprophytic yeasts at 1.5M. It has little effect on the growth of bacteria normally found in the vaginal flora.

EXAMPLE II

Assay for Candidistatic and Candidacidal Concentration of Glycerol

The standard turbidimetric assay for *C. albicans* growth was used. The Medium 19 broth based media were prepared from 10X Medium 19, glycerol and sterile water. Initially, the glycerol concentration varied from 0% to 75% in 23 increments. Turbidity was determined at 24, 28, and 48 hrs. At 48 hr., 0.20 ml was subcultured in regular Medium 19 broth. After 48 hr. incubation, growth of *C. albicans* was completely inhibited by 15% glycerol. Subculture documented that glycerol concentrations of >30% were Candidacidal.

The experiment was repeated several times with glycerol concentration ranging from 0% to 30% in 2.5% increments and over a 96 hour reaction interval. The data show that 15% glycerol caused a 50% suppression of Candida growth for 96 hours and glycerol was Candidacidal at 25%. The saprophytic yeast, *Saccharomyces cereviseae*, was less susceptible to suppression by glycerol and was not killed even at 30% glycerol concentration.

EXAMPLE III

Effect of Intermediates on Vaginal Organisms

The effect of key metabolic products of intermediate energy metabolism on growth of vaginal organisms was surveyed. Compared with either an inert buffer control or a PO$_4$ buffer control, pathogenic, opportunistic and saprophytic yeasts were strongly inhibited by 0.10M citrate at neutral pH and not effected by 0.10M lactate or succinate between pH 4.0 and pH 7.0. Growth of Staphylococci was inhibited by 75% by lactate, 40% by acetate and completely by citrate at neutral pH. The *E. coli* culture was partially inhibited by lactate and acetate. There is thus a marked difference in the effect of key metabolic intermediates on the yeast and bacteria associated with vaginal flora. Candida was very sensitive to acetic acid concentration, while, in comparison bacteria have little response at about pH 5 to pH 7.

EXAMPLE IV

Effect of pH on Growth of Vaginal Organisms

Respective samples of Medium 19 broth buffered with 200 mM 2-N-Morpholino]ethanesulfonic acid (MES), Na phosphate, Na acetate, Na citrate, and Na succinate were prepared. The appropriate amount of acidic and basic forms of the buffers were calculated to provide pH 4.0, 4.5, 5.0, 6.0, and 7.0 for 100 ml medium. 40 ml of water and 50 ml 2X Medium 19 broth were mixed and the pH determined. If necessary, the pH was adjusted with 1M NaOH or 1M HCl and the final volume was adjusted to 200 ml. The control medium for each buffer was a mixture of 5 ml of the respective pH 6.0 medium, 45 ml water and 50 ml 2X Medium 19 broth, made to equal ionic strength with NaCl. All media were steam sterilized.

A rack of cultures consisting of all six buffered media at each of the five pH values and a control was prepared to contain 9.9 ml/tube. One rack of buffer tubes was prepared for each organism, *C. albicans* (ATCC 14053), *C. albicans* (ATCC 38247), *C. tropicalis, C. stellatoidea, S. cerevisiae,* Streptomyces sp (ATCC 19950), *S. epidermidis,* and *E. coli.* Each tube was inoculated with 0.10 ml of the respective logarithmic phase culture diluted to $A_{600}=0.05$. The tubes were mixed well and incubated. The growth of the organisms was determined turbidimetrically at 600 nm at approximately 18, 24, 48, and 72 hours.

At the end of the incubation, the pH of the culture medium was determined. If there was no increase in turbidity by the final determination, 0.10 ml of the culture fluid was subcultured into regular Medium 19 broth, incubated and observed for growth after 48 hours.

A parallel experiment was done using the buffers diluted in MRS medium and inoculated with Lactobacillus sp (ATCC 9857).

Figure 4:
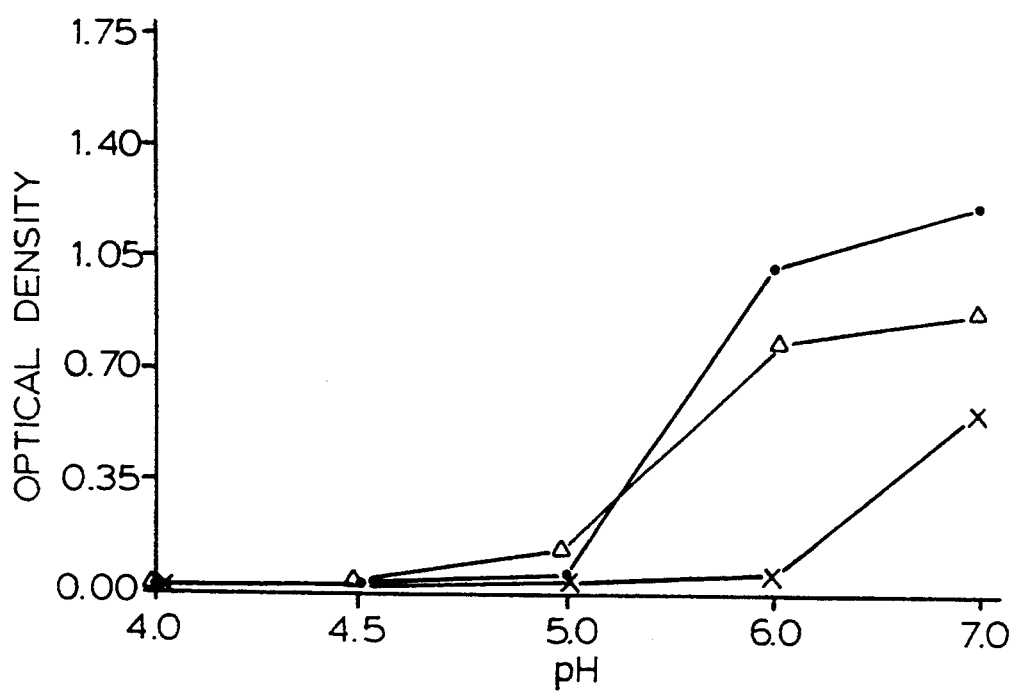
FIG. 4 is a graph of optical density ($A_{600}$) of Streptococcus (●), E. coli (x) and Lactobacillus (Δ) at different pH values of acetate after 23–30 hours.
Figure 5:
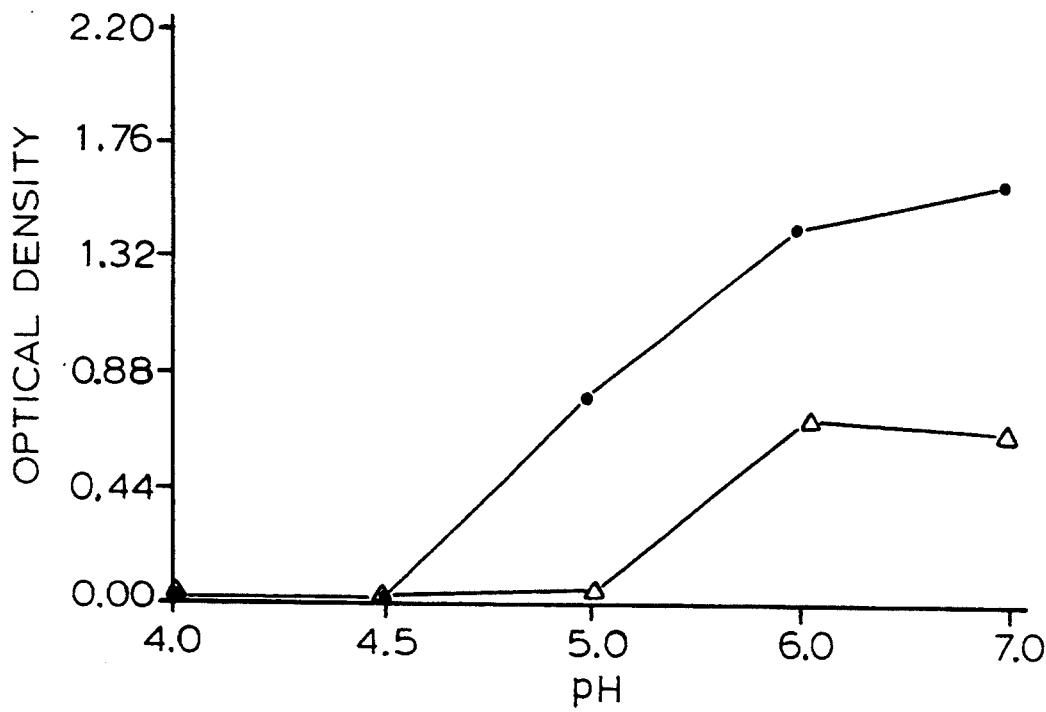
FIG. 5 is a graph of optical density ($A_{600}$) of C. tropicalis at different pH values of acetate at 24 (Δ) and 48 (●) hours.
Figure 6:
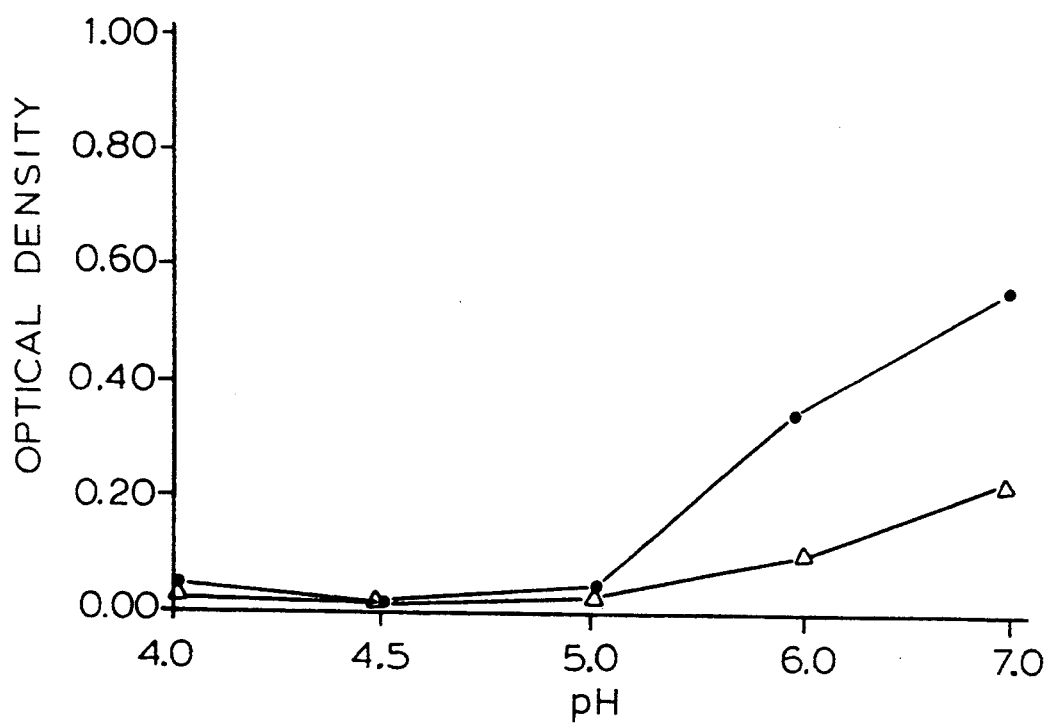
FIG. 6 is a graph of optical density ($A_{600}$) of C. stellatoidea at different pH values of acetate at 24 (Δ) and 48 (●) hours.
Figure 7:
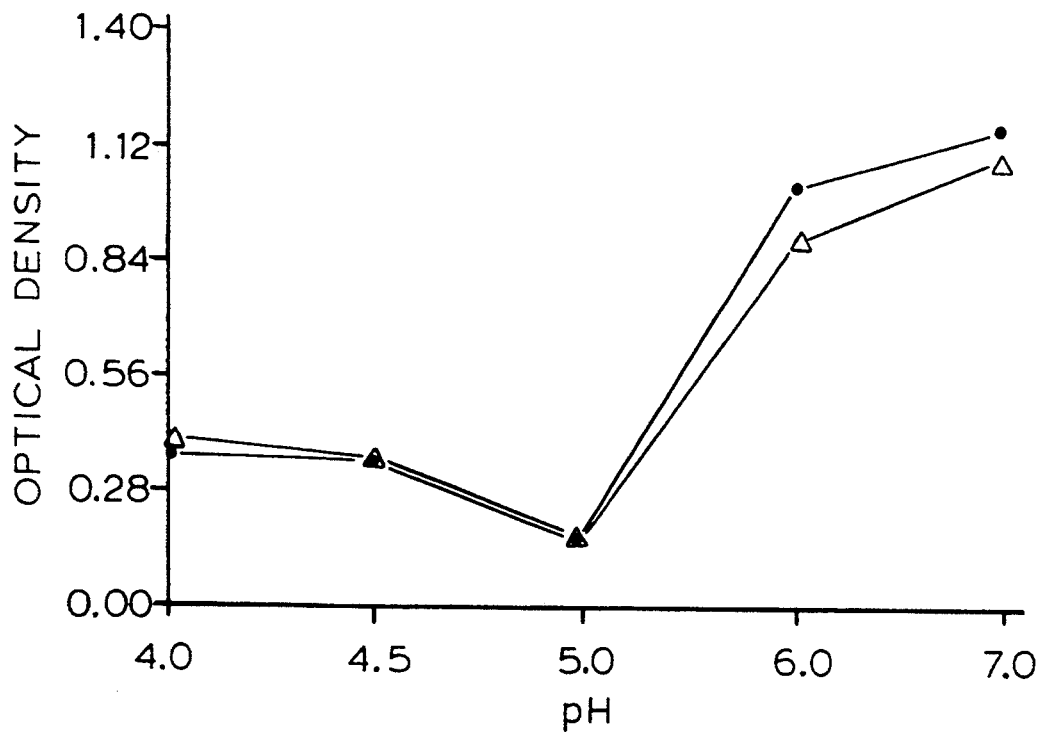
FIG. 7 is a graph of optical density ($A_{600}$) of C. albicans (strain 14053) at different pH values of acetate at 31 (Δ) and 46 (●) hours.
Figure 8:
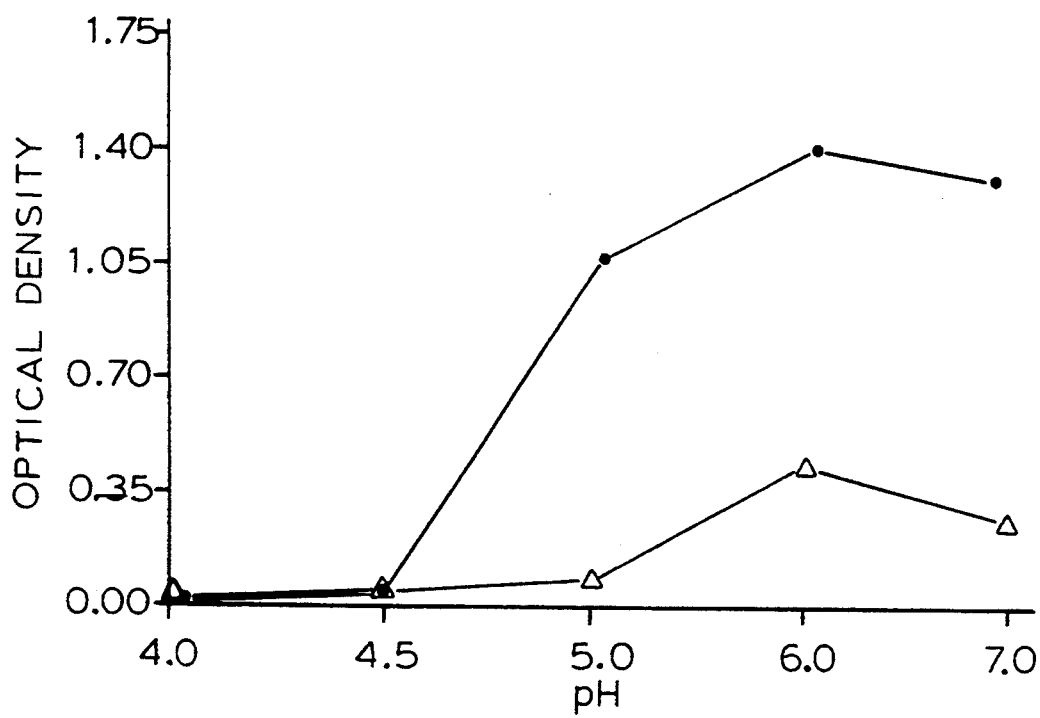
FIG. 8 is a graph of optical density ($A_{600}$) of S. cerevisiae at different pH values of acetate at 24 (Δ) and 43 (●) hours.

The results for *Candida albicans, S. cerevisiae,* and Lactobacillus are set forth below in Tables IV, V, and VI, respectively. The results for acetate are also shown graphically in the Figures as follows: for sampling at 23–30 hours post-infection for Streptococcus, *E. coli* and Lactobacillus (FIG. 4); and for sampling at 24–32 and 46–48 hours post-infection for *C. tropicalis, C. stellatoidea, C. albicans* (strain 14053) and *S. cerevisiae* (FIGS. 5–8 respectively). The results obtained with *Candida albicans* are generally representative of those obtained with the other Candida species, while the *S. cerevisiae* and Lactobacillus are generally representative of normal vaginal flora species.

TABLE IV

| BUFFER: | MES | | PO$_4$ | | CANDIDA LACTATE | | ACETATE | | SUCCINATE | | CITRATE | |
|---|---|---|---|---|---|---|---|---|---|---|---|---|
| Incubation Times, Hrs. | pH | Optical Density | pH | Optical Density | pH | Optical Density | pH | Optical Density | pH | Optical Density | pH | Optical Density |
| 18 | 4 | .457 | 4 | .427 | 4 | .249 | 4 | .018 | 4 | .506 | 4 | .811 |
| " | 4.5 | .553 | 4.5 | .432 | 4.5 | .46 | 4.5 | 3.000001E-03 | 4.5 | .661 | 4.6 | .662 |
| " | 5 | .599 | 5 | .41 | 5 | .581 | 5 | .048 | 5 | .661 | 5 | .165 |
| " | 6 | .679 | 6 | .36 | 6 | .651 | 6 | .275 | 6 | .776 | 6 | −.019 |
| " | 7 | .519 | 7 | 8.700001E-02 | 7 | .72 | 7 | .506 | 7 | .683 | 7 | .022 |
| " | 6.1 | .729 | 6.1 | .677 | 6.1 | .801 | 6.1 | .7290001 | 6.1 | .848 | 6.1 | 1.017 |
| 24 | 4 | 1.058 | 4 | .989 | 4 | .876 | 4 | .019 | 4 | 1.007 | 4 | 1.105 |
| " | 4.5 | 1.141 | 4.5 | .983 | 4.5 | 1.042 | 4.5 | .011 | 4.5 | 1.195 | 4.5 | 1.058 |
| " | 5 | 1.218 | 5 | 1.092 | 5 | 1.135 | 5 | .058 | 5 | 1.145 | 5 | .466 |
| " | 6 | 1.151 | 6 | .9690001 | 6 | 1.152 | 6 | .899 | 6 | 1.232 | 6 | .073 |
| " | 7 | 1.104 | 7 | .318 | 7 | 1.16 | 7 | .899 | 7 | 1.114 | 7 | .112 |
| " | 6.1 | 1.219 | 6.1 | 1.196 | 6.1 | 1.264 | 6.1 | 1.134 | 6.1 | 1.213 | 6.1 | 1.202 |
| 48 | 4 | 1.131 | 4 | 1.049 | 4 | 1.061 | 4 | .017 | 4 | 1.147 | 4 | 1.171 |
| " | 4.5 | 1.118 | 4.5 | 1.051 | 4.5 | 1.215 | 4.5 | 4.999999E-03 | 4.5 | 1.152 | 4.5 | 1.093 |
| " | 5 | 1.107 | 5 | 1.098 | 5 | 1.183 | 5 | .056 | 5 | 1.211 | 5 | .8839999 |
| " | 6 | 1.241 | 6 | 1.078 | 6 | 1.237 | 6 | .809 | 6 | 1.13 | 6 | .492 |
| " | 7 | 1.085 | 7 | 1.1 | 7 | 1.199 | 7 | .897 | 7 | 1.129 | 7 | .614 |
| " | 6.1 | 1.266 | 6.1 | 1.104 | 6.1 | 1.173 | 6.1 | 1.173 | 6.1 | 1.266 | 6.1 | 1.204 |
| 72 | 4 | 1.294 | 4 | 1.164 | 4 | 1.052 | 4 | .015 | 4 | 1.156 | 4 | 1.391 |
| " | 4.5 | 1.315 | 4.5 | 1.062 | 4.5 | 1.198 | 4.5 | .011 | 4.5 | 1.269 | 4.5 | 1.259 |
| " | 5 | 1.246 | 5 | 1.305 | 5 | 1.267 | 5 | .057 | 5 | 1.377 | 5 | .8300001 |
| " | 6 | 1.436 | 6 | 1.195 | 6 | 1.371 | 6 | .786 | 6 | 1.324 | 6 | .651 |
| " | 7 | 1.202 | 7 | 1.292 | 7 | 1.261 | 7 | .862 | 7 | 1.313 | 7 | .657 |
| " | 6.1 | 1.359 | 6.1 | 1.233 | 6.1 | 1.268 | 6.1 | 1.58 | 6.1 | 1.314 | 6.1 | 1.485 |

TABLE V

| BUFFER: | MES | | PO$_4$ | | *S. cerevisiae* LACTATE | | ACETATE | | SUCCINATE | | CITRATE | |
|---|---|---|---|---|---|---|---|---|---|---|---|---|
| Incubation Times, Hrs. | pH | Optical Density | pH | Optical Density | pH | Optical Density | pH | Optical Density | pH | Optical Density | pH | Optical Density |
| 18 | 4 | .038 | 4 | .046 | 4 | .035 | 4 | .034 | 4 | .041 | 4 | .048 |
| " | 4.5 | .089 | 4.5 | .08 | 4.5 | .044 | 4.5 | .005 | 4.5 | .084 | 4.5 | .032 |
| " | 5 | .063 | 5 | .072 | 5 | .092 | 5 | .053 | 5 | .061 | 5 | .028 |
| " | 6 | .069 | 6 | .066 | 6 | .045 | 6 | .045 | 6 | .052 | 6 | .024 |
| " | 7 | .057 | 7 | .11 | 7 | .044 | 7 | .042 | 7 | .071 | 7 | .01 |
| " | 6 | .06 | 6 | .064 | 6 | .043 | 6 | .07 | 6 | .075 | 6 | .057 |
| 24 | 4 | .386 | 4 | .408 | 4 | .391 | 4 | .035 | 4 | .373 | 4 | .399 |
| " | 4.5 | .441 | 4.5 | .467 | 4.5 | .411 | 4.5 | .018 | 4.5 | .481 | 4.5 | .345 |
| " | 5 | .488 | 5 | .498 | 5 | .56 | 5 | .084 | 5 | .471 | 5 | .007 |
| " | 6 | .523 | 6 | .526 | 6 | .474 | 6 | .438 | 6 | .488 | 6 | .01 |
| " | 7 | .398 | 7 | .213 | 7 | .457 | 7 | .257 | 7 | .384 | 7 | .019 |
| " | 6 | .526 | 6 | .515 | 6 | .522 | 6 | .536 | 6 | .466 | 6 | .456 |
| 48 | 4 | 1.53 | 4 | 1.537 | 4 | 1.503 | 4 | .021 | 4 | 1.493 | 4 | 1.512 |
| " | 4.5 | 1.57 | 4.5 | 1.565 | 4.5 | 1.529 | 4.5 | 8.000001E-03 | 4.5 | 1.548 | 4.5 | 1.442 |
| " | 5 | 1.566 | 5 | 1.54 | 5 | 1.556 | 5 | 1.052 | 5 | 1.506 | 5 | .227 |
| " | 6 | 1.591 | 6 | 1.554 | 6 | 1.529 | 6 | 1.409 | 6 | 1.528 | 6 | .001 |
| " | 7 | 1.536 | 7 | 1.314 | 7 | 1.551 | 7 | 1.33 | 7 | 1.468 | 7 | .014 |
| " | 6 | 1.616 | 6 | 1.576 | 6 | 1.579 | 6 | 1.57 | 6 | 1.585 | 6 | 1.529 |
| 72 | 4 | 1.509 | 4 | 1.51 | 4 | 1.561 | 4 | .025 | 4 | 1.529 | 4 | 1.519 |
| " | 4.5 | 1.53 | 4.5 | 1.523 | 4.5 | 1.527 | 4.5 | .299 | 4.5 | 1.497 | 4.5 | 1.452 |
| " | 5 | 1.549 | 5 | 1.519 | 5 | 1.54 | 5 | 1.212 | 5 | 1.499 | 5 | .359 |
| " | 6 | 1.505 | 6 | 1.481 | 6 | 1.536 | 6 | 1.408 | 6 | 1.496 | 6 | .053 |
| " | 7 | 1.521 | 7 | 1.48 | 7 | 1.523 | 7 | 1.456 | 7 | 1.495 | 7 | .021 |
| " | 6 | 1.542 | 6 | 1.557 | 6 | 1.629 | 6 | 1.555 | 6 | 1.538 | 6 | 1.514 |

TABLE VI

| BUFFER: | MES | | PO$_4$ | | LACTOBACILLUS LACTATE | | ACETATE | | SUCCINATE | | CITRATE | |
|---|---|---|---|---|---|---|---|---|---|---|---|---|
| Incubation Times, Hrs. | pH | Optical Density | pH | Optical Density | pH | Optical Density | pH | Optical Density | pH | Optical Density | pH | Optical Density |
| 18 | 4 | 0 | 4 | 0 | 4 | 0 | 4 | 0 | 4 | 0 | 4 | 0 |
| " | 4.5 | 0 | 4.5 | 8.999999-03 | 4.5 | 0 | 4.5 | 0 | 4.5 | .083 | 4.5 | .002 |
| " | 5 | .039 | 5 | .069 | 5 | .061 | 5 | .029 | 5 | .112 | 5 | .046 |
| " | 6 | .142 | 6 | .159 | 6 | .23 | 6 | 9.000001E-02 | 6 | .206 | 6 | .153 |
| " | 7 | .331 | 7 | .322 | 7 | .79 | 7 | .246 | 7 | .371 | 7 | .349 |
| 24 | 4 | 0 | 4 | 0 | 4 | 0 | 4 | 0 | 4 | 0 | 4 | 0 |
| " | 4.5 | .004 | 4.5 | .01 | 4.5 | .005 | 4.5 | 0 | 4.5 | .042 | 4.5 | .006 |
| " | 5 | .054 | 5 | .081 | 5 | .078 | 5 | .032 | 5 | .109 | 5 | .058 |
| " | 6 | .176 | 6 | .172 | 6 | .252 | 6 | .106 | 6 | .198 | 6 | .172 |
| " | 7 | .984 | 7 | .347 | 7 | .796 | 7 | .269 | 7 | .376 | 7 | .368 |
| 48 | 4 | 0 | 4 | 0 | 4 | 0 | 4 | 0 | 4 | .006 | 4 | 0 |

TABLE VI-continued

| BUFFER: | MES | | PO4 | | LACTOBACILLUS LACTATE | | ACETATE | | SUCCINATE | | CITRATE | |
|---|---|---|---|---|---|---|---|---|---|---|---|---|
| Incubation Times, Hrs. | pH | Optical Density | pH | Optical Density | pH | Optical Density | pH | Optical Density | pH | Optical Density | pH | Optical Density |
| " | 4.5 | .052 | 4.5 | .021 | 4.5 | .077 | 4.5 | .002 | 4.5 | .052 | 4.5 | .023 |
| " | 5 | .733 | 5 | .13 | 5 | .61 | 5 | .119 | 5 | .177 | 5 | .103 |
| " | 6 | 1.208 | 6 | .842 | 6 | .967 | 6 | .798 | 6 | .823 | 6 | .2 |
| " | 7 | .984 | 7 | .897 | 7 | 1.224 | 7 | .921 | 7 | .892 | 7 | .424 |
| 72 | 4 | 0 | 4 | 0 | 4 | 8.000001E-02 | 4 | 0 | 4 | .004 | 4 | 8.999999E-03 |
| " | 4.5 | 1.393 | 4.5 | .027 | 4.5 | 1.354 | 4.5 | .051 | 4.5 | .117 | 4.5 | .082 |
| " | 5 | 1.759 | 5 | 1.085 | 5 | 1.702 | 5 | 1.647 | 5 | 1.574 | 5 | .111 |
| " | 6 | 2.111 | 6 | 1.917 | 6 | 2.056 | 6 | 1.783 | 6 | 1.887 | 6 | .245 |
| " | 7 | 2.248 | 7 | 1.954 | 7 | 2.044 | 7 | 1.891 | 7 | 1.86 | 7 | .456 |

Growth of the yeasts was generally not affected by pH in the range 4.5 to 7.0. Representative bacterial flora associated with the vaginal tract were strongly inhibited by acid pH and growth was nearly completely inhibited below pH 6.0. A pH of 4.5 was inhibitory for most of the bacteria. The acetate buffer at pH 4.0 and 4.5 was inhibitory for all three Candida species tested.

EXAMPLE V

Effect of Acetate/Acetic Acid Concentration on Growth of Vaginal Organisms

A stock of 2M acetate buffer was prepared at pH 7.0 and 4.5. Two sets of tubes, one at pH 4.5 and one at pH 7.0, was prepared for each organism. One tube of each set contained a final concentration of acetate at 1 mM, 5 mM, 10 mM, 50 mM, 100 mM, 500 mM, and 1000 mM. A 4X preparation of Medium 19 broth was added to the proper volume of acetate buffer and diluted to a final volume of 9.9 ml experimental medium at 1X. The salts in the medium with 100 mM acetate were adjusted to 100 mM with NaCl; then those with 100 mM acetate were adjusted to 1000 mM with NaCl.

One set of media was inoculated with each of *C. albicans* (wt), *C. tropicalis*, *S. cerevisiae*, *S. epidermidis*, and *E. coli*. The inoculum was 0.10 ml of a logarithmic phase culture diluted to $A_{600}=0.05$ with Medium 19 broth. Each tube was mixed well and incubated. Growth was determined turbidimetrically at 600 nm after 10, 16, 39, and 60 hrs. incubation. Cultures with no increase in turbidity at 600 nm were subcultured into regular Medium 19 broth and observed for growth after incubation for 48 hrs.

Data obtained during these tests for cultures of *Candida albicans* and *S. cereviseae* are set out in Tables VII and VIII below.

TABLE VII

| | CANDIDA | | | |
|---|---|---|---|---|
| pH: Incubation Times, Hrs. | 4.5 | | 7.0 | |
| | Concentration, mM | Optical Density | Concentration, mM | Optical Density |
| 10 | 1 | .121 | 1 | .184 |
| " | 5 | .115 | 5 | .19 |
| " | 10 | .09 | 10 | .178 |
| " | 50 | .023 | 50 | .175 |
| " | 100 | .02 | 100 | .159 |
| " | 500 | .034 | 500 | .085 |
| " | 1000 | .05 | 1000 | .122 |
| 16 | 1 | .664 | 1 | .836 |
| " | 5 | .539 | 5 | .827 |
| " | 10 | .464 | 10 | .789 |
| " | 50 | .028 | 50 | .748 |
| " | 100 | .021 | 100 | .737 |
| " | 500 | .029 | 500 | .111 |
| " | 1000 | .044 | 1000 | .124 |
| 39 | 1 | 1.302 | 1 | 1.393 |
| " | 5 | 1.377 | 5 | 1.406 |
| " | 10 | 1.217 | 10 | 1.406 |
| " | 50 | .093 | 50 | 1.234 |
| " | 100 | .024 | 100 | 1.225 |
| " | 500 | .031 | 500 | .222 |
| " | 1000 | .053 | 1000 | .135 |
| 60 | 1 | 1.591 | 1 | 1.787 |
| " | 5 | 1.63 | 5 | 1.817 |
| " | 10 | 1.5 | 10 | 1.645 |
| " | 50 | .212 | 50 | 1.494 |
| " | 100 | .042 | 100 | 1.228 |
| " | 500 | .048 | 500 | .373 |
| " | 1000 | .071 | 1000 | .158 |

TABLE VIII

| | S. CEREVISIAE | | | |
|---|---|---|---|---|
| pH: Incubation Times, Hrs. | 4.5 | | 7.0 | |
| | Concentration, mM | Optical Density | Concentration, mM | Optical Density |
| 10 | 1 | .036 | 1 | .051 |
| " | 5 | .038 | 5 | .052 |
| " | 10 | .034 | 10 | .053 |
| " | 50 | .029 | 50 | .061 |
| " | 100 | .028 | 100 | .065 |
| " | 500 | .034 | 500 | .087 |
| " | 1000 | .05 | 1000 | .12 |
| 16 | 1 | .129 | 1 | .121 |
| " | 5 | .127 | 5 | .134 |
| " | 10 | .058 | 10 | .129 |
| " | 50 | .058 | 50 | .135 |
| " | 100 | .029 | 100 | .129 |
| " | 500 | .023 | 500 | .077 |
| " | 1000 | .044 | 1000 | .113 |
| 39 | 1 | 1.541 | 1 | 1.542 |
| " | 5 | 1.518 | 5 | 1.545 |
| " | 10 | 1.445 | 10 | 1.523 |
| " | 50 | 1.166 | 50 | 1.542 |
| " | 100 | .128 | 100 | 1.4 |
| " | 500 | .042 | 500 | .232 |
| " | 1000 | .046 | 1000 | .136 |
| 60 | 1 | 1.545 | 1 | 1.536 |
| " | 5 | 1.546 | 5 | 1.543 |
| " | 10 | 1.489 | 10 | 1.569 |
| " | 50 | 1.281 | 50 | 1.445 |
| " | 100 | .254 | 100 | 1.445 |
| " | 500 | .032 | 500 | .093 |
| " | 1000 | .061 | 1000 | .129 |

Growth of the pathogenic *C. albicans* was 85% inhibited by 50 mM acetate buffer at pH 4.5 and essentially completely inhibited at 100 mM acetate buffer at pH 4.5. The acetate buffer at pH 7.0 had little effect. The growth of the nonpathogenic yeast was suppressed by 100 mM acetate buffer at pH 4.5. The acetate buffer at pH 7.0 had no effect on the growth of saprophytic yeast. The concentration of the acetate buffer per se had no effect on the growth of the representative vaginal bacteria.

EXAMPLE VI

Effect of Citrate Concentration on Growth of Vaginal Organisms

A stock of 4M citrate buffer was prepared at pH 7.0 and 4.5. Two sets of tubes, one at pH 4.5 and one at pH 7.0, were prepared for each organism. One tube of each set contained a final concentration of citrate at 1 mM, 5 mM, 10 mM, 50 mM, 100 mM, 500 mM, and 1000 mM. A 4X preparation of Medium 19 broth was added to the proper volume of citrate buffer and diluted to a final volume of 9.9 ml experimental medium at 1X. The salts in the medium with 100 mM were adjusted to 200 mM with NaCl; those with 100 mM citrate were adjusted to 2000 mM with NaCl.

The sets of medium at pH 4.5 and 7.0 were inoculated with each of $C.$ $albicans$ (wt), $C.$ $tropicalis$, $S.$ $cerevisiae$, $S.$ $epidermis$, and $E.$ $coli$. The inoculum was 0.10 ml of a logarithmic phase culture diluted to $A_{600}=0.05$ with Medium 19 broth. Each tube was mixed well and incubated. Growth was determined turbidimetrically at 600 nm after 10, 16, 39, and 60 hours incubation. Cultures with no increase in turbidity at 600 nm were subcultured into regular Medium 19 broth and observed for growth after incubation for 48 hours.

The representative species of vaginal bacteria were much more sensitive to citrate concentration than $C.$ $albicans$. The saprophytic yeasts were not effected by the citrate levels. Concentrations of citrate $>500$ mM at either pH 7.0 or pH 4.5 were inhibitory for $C.$ $albicans$.

The foregoing tests and data show the efficacy of the compositions according to the present invention comprising an active yeast-inhibitory agent in combination with a neutral buffering solution. The compositions of the invention produce a fungistatic and/or fungicidal action on the various Candida species, and are highly effective in the treatment of Monilia infections of the vagina. The neutral buffering of the composition of the invention permits vaginal flora to experience high growth rate, serving to effectively establish the normal biota of the vagina, following which its pH condition, as a result of metabolite accumulations, is gradually reduced to normal levels on the order of about 4.5, where increased concentration of the nonionized buffer compound further enhances the inhibitory activity of the composition. To the extent that the metabolic by-products are effective in inhibiting the Candida species, the overall effectiveness of the composition is still further enhanced.

EXAMPLE VII

Effect of Acetate Esters on Candida

Figure 2:
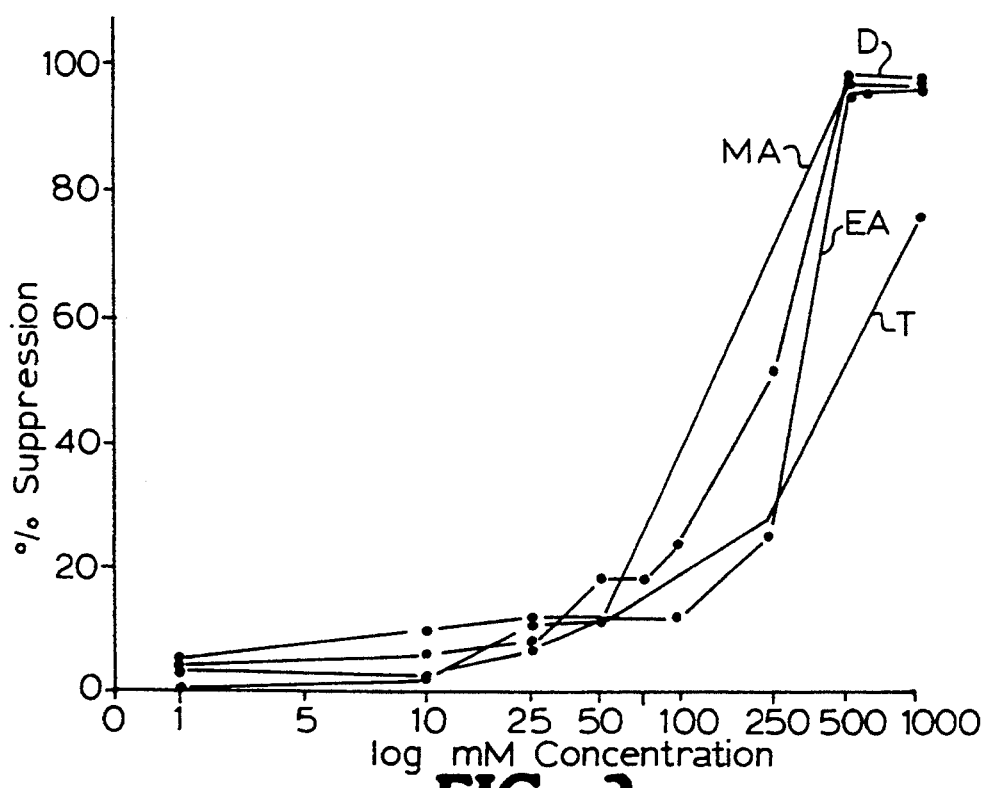
FIG. 2 is a graph of percent suppression of Candida at various concentrations of diacetin (D), methylacetate (MA), ethylacetate (EA) and triacetin (T).

Medium 19 tubes containing varying levels of methyl acetate, ethyl acetate, diacetin or triacetin at about pH 7.0 were inoculated with $C.$ $albicans$ strains as described in Example VI, and turbidity was determined periodically for 96 hours incubation. The results at 24 hours, an example of which is shown in FIG. 2 as percent suppression as compared to controls, indicate an inhibitory effect of each ester as compared to growth on Medium 19 alone.

EXAMPLE VIII

Effect of Serum on Glycerol Inhibition

Figure 3:
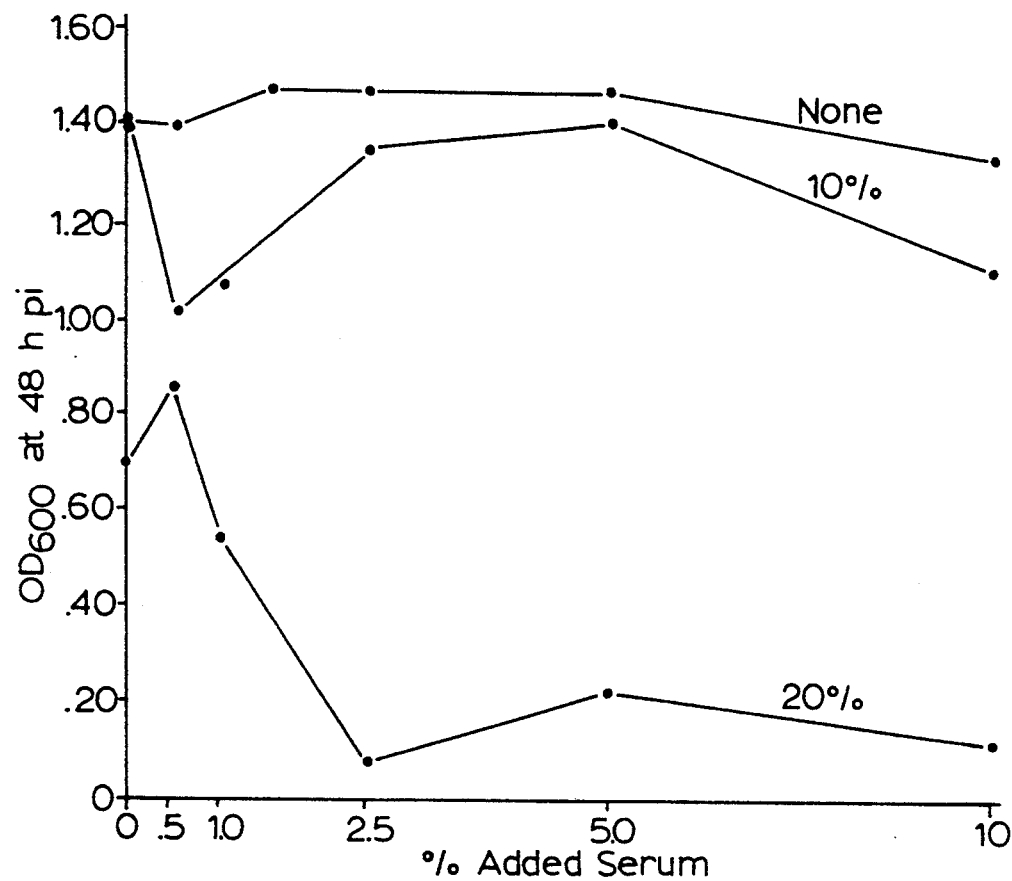
FIG. 3 is a graph of optical density (A) of Candida versus percent added serum at 0%, 10%, and 20% glycerol.

Since transudation and exudation is characteristic of inflammatory reactions and is frequently present in yeast infections, the impact of serum on the ability of glycerol to inhibit yeast growth was determined. Serum concentrations from 0% to 10% were evaluated. Three types of Medium 19 broth were prepared: regular; 10% glycerol added; and 20% glycerol added. Two sets of six culture tubes were prepared for each type of medium. To each medium, 0%, 0.5%, 1.0%, 2.5%, 5.0% or 10% calf serum was added to a tube of the series and the final volume was 9.9 ml. Each tube was inoculated with 0.10 ml logarithmic phase $C.$ $albicans$ or $S.$ $cerevisiae$. The amount of growth was determined by turbidimetric assay at 600 nm at 16, 20, 40, and 48 hrs. FIG. 3 shows the results with Candida. A range of serum from 0 to 10% did not alter the inhibition of Candida or Saccharomyces growth by 0 to 10% glycerol but increased the inhibition at 20% glycerol.

EXAMPLE IX

Effect of Nystatin on Yeast

Nystatin USP (Paddock Laboratories, Minneapolis, Minn.) was dissolved in dimethyl formamide (DMF) at a concentration to 10 mg/ml DMF. The putative activity was 5830 $\mu$/mg. A set of 10 assay tubes containing 9.9 ml Medium 19 was prepared. A range of 1 to 100 units/ml final concentration of Nystatin was added to the medium in a total of 100 $\mu$l DMF. Controls containing 100 $\mu$l pure DMF and no DMF were also included. Each tube was mixed well and inoculated with 0.10 ml of logarithmic phase $C.$ $albicans$ or $S.$ $cerevisiae$. The assays were incubated in the dark, $C.$ $albicans$ at 37° C., $S.$ $cerevisiae$ at 25° C. The turbidity of the cultures was determined at 24, 48, and 72 hours and at 7 days. All assay tubes were subcultured at 96 hours by transferring 0.10 ml to regular medium 19 broth and incubating for 48 hours.

A concentration of 1 unit Nystatin/ml completely inhibited Saccharomyces at 72 hours and caused 50% suppression after 7 days incubation. Concentrations $>1.5$ units Nystatin/ml killed this saprophytic yeast. Concentrations $>2.5$ units Nystatin/ml were inhibitory to Candida. Candida was 99% inhibited by 2.5 units Nystatin/ml at 48 hours but only 10% at 72 hours. Saprophytic yeast appear to be killed by about half the Nystatin concentration required to kill $C.$ $albicans$.

The effect of having 10% glycerol at the various Nystatin concentrations in Medium 19 was to increase the inhibition of Candida. Thus, at any one sampling time, in the presence of glycerol, a lower concentration of Nystatin resulted in the same inhibitory effect as a higher level of Nystatin without glycerol.

Other anti-yeast antibiotics, such as clotrimazole, miconazole, butoconazole and terconazole may be used instead of Nystatin to augment anti-yeast activity of the composition of the invention.

While the invention has been described in detail with respect to specific embodiments of the invention, it will be readily apparent that other embodiments, modifications, and variations may be effectively employed, and accordingly, all such embodiments, modifications, and variations are to be regarded as being within the spirit and scope of the invention.

What is claimed is:

1. A composition for use as a vaginal cleanser and for the treatment of vaginal yeast while not adversely affecting normal vaginal bacterial growth, comprising:
   (a) a medically acceptable active yeast-inhibitory agent selected from one or more members of the group consisting of ethylene glycol, propylene glycol, and glycerol, having an effective concentration at the vaginal treatment site of at least 8% by volume of the composition volume plus the volume of other liquids present at the treatment site; and
   (b) an effectively buffered aqueous acetate solution said composition having a concentration of 10–500 mM acetate, said acetate being selected from the group consisting of diacetin, triacetin, compounds of the formula $CH_3COOR$ where R is selected from the group consisting of hydrogen and $C_1$–$C_3$ alkyl moieties, and salts of acetic acid;
wherein the concentration of acetate in said effectively buffered aqueous solution is effective to establish the pH of the composition in the range from pH 5.01 to about pH 7, and wherein the active yeast-inhibitory agent and said effectively buffered aqueous acetate solution are in selected proportions relative to one another effective to allow the active yeast-inhibitory agent to be inhibitory against vaginal yeast of the genus Candida, wherein growth of vaginal bacteria is enhanced as compared to growth of said bacteria at a normal vaginal pH, and wherein undesirable vaginal yeast cells are inhibited more than Saccharomyces yeast cells by said composition.

2. A composition according to claim 1, wherein the active yeast-inhibitory agent is propylene glycol.

3. A composition according to claim 1, wherein the active yeast-inhibitory agent is glycerol.

4. A composition according to claim 1, wherein the effective concentration of the active yeast-inhibitory agent at the treatment site is from about 8% to about 40% by volume, based on the total volume of components of (a) and (b).

5. A composition according to claim 1, wherein said acetate compound in said aqueous acetate solution is selected from the group consisting of acetic acid and salts of acetic acid.

6. A composition according to claim 1, wherein the acetate compound in said aqueous acetate solution is methyl acetate.

7. A composition according to claim 1, wherein the acetate compound is selected from the group consisting of ethyl acetate, diacetin, and triacetin.

8. A composition according to claim 1, further comprising an antibiotic effective against yeast.

9. A composition according to claim 8, wherein the antibiotic is selected from the group consisting of Nystatin, clotrimazole, miconazole, butoconazole and terconazole.

10. A composition according to claim 1, further comprising a means for maintaining an effective concentration of the composition in the vagina.

11. A composition according to claim 10, wherein the means for maintaining an effective concentration of the composition comprises a thickener in sufficient amount to enhance the vaginal retention of the composition subsequent to its intravaginal administration.

12. A composition according to claim 11, wherein said thickener is selected from the group consisting of hydroxymethylcellulose, hydroxymethylpropylcellulose, and carboxy methylcellulose.

13. A method for treatment of vaginal yeast while not adversely affecting normal vaginal bacterial growth, comprising applying to the vaginal locus a Candidacidally effective amount of a composition according to claim 1.

14. A composition for the treatment of vaginal yeast while not adversely affecting normal vaginal bacterial growth and being capable of enhancing growth of vaginal bacteria as compared to growth of said bacteria at a normal vaginal pH, comprising a solution comprising one or more medically acceptable agents selected from the group consisting of ethylene glycol, propylene glycol, glycerol, acetate derivatives of glycerol, and acetate; said solution having active yeast-inhibitory activity and being effectively buffered with 10–500 mM acetate to establish the pH of the composition at pH 5.01 to about pH 7, said acetate being selected from the group consisting of diacetin, triacetin and compounds of the formula $CH_3COOR$ where R is selected from the group consisting of diacetin, triacetin and compounds of the formula $CH_3COOR$ where R is selected from the group consisting of hydrogen and $C_1$–$C_3$ alkyl moieties.

15. A composition for use as a vaginal cleanser and for the treatment of vaginal yeast while not adversely affecting normal vaginal bacterial growth, comprising an effectively buffered aqueous acetate solution, said composition having a concentration of 10–500 mM acetate, said acetate being selected from the group consisting of diacetin, triacetin, compounds of the formula $CH_3COOR$ where R is selected from the group consisting of hydrogen and $C_1$–$C_3$ alkyl moieties, and salts of acetic acid; wherein the concentration of acetate in said effectively buffered aqueous solution is effective to establish the pH of the composition in the range from pH 5.01 to about pH 7, and wherein the effectively buffered aqueous acetate solution is inhibitory against vaginal yeast of the genus Candida, wherein growth of vaginal bacteria is enhanced as compared to growth of said bacteria at a normal vaginal pH, and wherein undesirable vaginal yeast cells are inhibited more than Saccharomyces yeast cells by said composition.

16. A method of allowing normal vaginal flora to be restored, comprising douching with a buffered acetate solution, said acetate solution having a concentration of 10–500 mM acetate to maintain the vaginal pH in the range of from pH 5.01 to about pH 7, for sufficient time to permit flushing of the vagina while permitting normal bacterial growth to occur in the vagina and enhancing growth of vaginal bacteria as compared to growth of said bacteria at a normal vaginal pH.

17. A method of allowing normal vaginal flora to be restored, comprising douching with an effectively buffered aqueous acetate solution, said solution buffered to maintain the vaginal pH in the range of from pH 5.01 to about pH 7, for sufficient time to permit flushing of the vagina while permitting normal bacterial growth to occur in the vagina and enhancing growth of vaginal bacteria as compared to growth of said bacteria at a normal vaginal pH, said acetate being at a concentration of 10–500 mM and being selected from the group consisting of diacetin, triacetin, compounds of the formula $CH_3COOR$ where R is selected from the group consisting of hydrogen and $C_1$–$C_3$ alkyl moieties and salts of acetic acid.

18. A method of allowing normal vaginal flora to be restored, comprising douching with a buffered solution of a yeast-inhibitory agent, said yeast-inhibitory agent selected from one or more members of the group consisting of ethylene glycol, propylene glycol, and glycerol, said solution buffered with 10–500mM acetate to maintain the vaginal pH in the range of from pH 5.01 to about pH 7, for sufficient time to permit flushing of the vagina while permitting normal bacterial growth to occur in the vagina and enhancing growth of vaginal bacteria as compared to growth of said bacteria at a normal vaginal pH.

19. A method for treatment of vaginal yeast while not adversely affecting normal vaginal bacterial growth, comprising applying to the vaginal locus a buffered solution of a yeast-inhibitory agent in an amount effective to inhibit Candida, said yeast-inhibitory agent selected from one or more members of the group consisting of ethylene glycol, propylene glycol, and glycerol, said solution buffered with acetate at a concentration of 10–500 mM to maintain the vaginal pH in the range of from pH 5.01 to about pH 7, for sufficient time to permit the yeast-inhibitory agent to inhibit the vaginal yeast while permitting normal bacterial growth to occur in the vaginal locus, and enhancing growth of vaginal bacteria as compared to growth of said bacteria at a normal vaginal pH, and then permitting the vaginal pH to decline to an acidic condition in the vicinity of pH 4.5.

* * * * *